United States Patent [19]

Meszàros Grechke et al.

[11] Patent Number: 5,079,355

[45] Date of Patent: Jan. 7, 1992

[54] PROCESS FOR THE SYNTHESIS OF POLYOL FATTY ACID POLYESTERS

[75] Inventors: Yulir Meszàros Grechke, The Hague; Pleun van der Plank, Huizen; Adrianus Rozendaal, Vlaardingen, all of Netherlands

[73] Assignee: Van den Bergh Foods Co., Division of Conopco, Inc., New York, N.Y.

[21] Appl. No.: 293,254

[22] Filed: Jan. 4, 1989

[30] Foreign Application Priority Data

Jan. 5, 1988 [GB] United Kingdom .................. 8800087

[51] Int. Cl.$^5$ ...................... C07H 13/00; C07H 1/00; C08B 37/00
[52] U.S. Cl. .................................... 536/119; 536/115; 536/124; 260/398; 260/410; 260/410.6
[58] Field of Search ............... 536/119, 115, 124, 120, 536/116, 127; 260/398, 410, 410.6

[56] References Cited

U.S. PATENT DOCUMENTS

| | | | |
|---|---|---|---|
| 3,963,699 | 6/1976 | Rizzi et al. | 260/410.6 |
| 4,517,360 | 5/1985 | Volpenhein | 536/119 |
| 4,518,772 | 5/1985 | Volpenhein | 536/119 |

FOREIGN PATENT DOCUMENTS 0132293  1/1985  European Pat. Off. ............ 536/119

Primary Examiner—Ronald W. Griffin
Assistant Examiner—Everett White
Attorney, Agent, or Firm—Gerard J. McGown

[57] ABSTRACT

The invention pertains to a process for the synthesis of polyol fatty acid polyesters involving transesterification of a reaction mixture comprising a soap emulsifier in which during the reaction at a degree of conversion within the range of from 15 to 60% the soap level is substantially reduced. By this process the high-viscosity and separating-out problems attached to the soap emulsifier in the later stages of the reaction are avoided.

10 Claims, No Drawings

PROCESS FOR THE SYNTHESIS OF POLYOL FATTY ACID POLYESTERS

The present invention relates to a process for the synthesis of polyol fatty acid polyesters wherein a substantially solvent-free reaction mixture of a polyol and/or fatty acid oligoesters thereof, a fatty acid lower-alkylester, a transesterification catalyst, and an emulsifier selected from the group of alkali metal soaps, is caused to react under transesterification conditions. Particularly, but not exclusively the invention relates to a process for the synthesis of sugar fatty acid polyesters, such as sucrose fatty acid polyesters.

By "polyol" is meant any aliphatic or aromatic compound which comprises at least four free hydroxyl groups. In particular such polyols include the group of sugar polyols, which comprise the sugars, i.e. the mono-, di- and polysaccharides, the corresponding sugar alcohols and the derivatives thereof having at least four free hydroxyl groups. Examples of sugar polyols include glucose, mannose, galactose, xylose, fructose, sorbose, tagatose, ribulose, xylulose, lactose, maltose, raffinose, cellobiose, sucrose, erythritol, mannitol, lactitol, sorbitol, xylitol and α-methylglucoside. A generally used sugar polyol is sucrose.

In this specification by "polyol fatty acid ester" is meant any such polyesters or mixtures thereof having a degree of conversion of at least 90%. The degree of conversion is defined as the percentage of polyol hydroxyl groups of the polyol fatty acid polyester that on an average have been esterified with fatty acids, a degree of conversion of 100% corresponding to the fully esterified polyol.

In this specification by "fatty acid" is meant $C_8$–$C_{24}$ fatty acids which may be saturated or unsaturated, and may have straight or branched alkyl chains.

The polyol fatty acid polyesters are known to be suitable low-calorie fat-replacers in edible products. Substantially indigestible for human beings they have physical and organoleptic properties very similar to triglyceride oils and fats conventionally used in edible products. Polyol fatty acid polyesters are further reported to have use as pharmaceutical agents in view of their ability to take up fat-soluble substances, such as in particular cholesterol, in the gastro-intestinal tract, and subsequently remove these substances from the human body.

In general polyol fatty acid polyesters are synthesized by a process in which a polyol, such as a mono- or disaccharide, is reacted with a fatty acid lower-alkylester, often the fatty acid methylester, in the presence of a transesterification catalyst, such as e.g. an alkali metal hydroxide or carbonate. In a first stage a polyol fatty acid mono- or oligoester is formed, which in a second stage after subsequent addition of further fatty acid lower-alkylester is reacted to form polyesters of the desired degree of conversion. Under certain conditions the two stages of the reaction can be combined into a single reaction.

Processes of this type are described in e.g. the U.S. Pat. Nos. 3,963,699, 4,517,360, and 4,518,772.

An often necessary component in the initially heterogeneous reaction mixture is an emulsifying or dispersing agent, such as in particular the alkali metal soaps. Although essential in the initial phase of the transesterification reaction, soap causes a number of problems towards the end of the reaction, in particular when the reaction is carried out on a technical scale. A major problem is that with increasing degrees of conversion to polyester, soap tends to separate-out resulting in a high viscosity of the reaction mixture and consequently poor mixing, slow release of the lower-alkyl alcohol and therefore prolonged reaction times.

A further problem connected to the separating-out of the soap emulsifier is that of soap deposition on equipment parts, such as the reaction vessel.

It has now been found that the above problems can essentially be overcome by removing the soap from the reaction mixture at a degree of conversion where its emulsifying properties are not required anymore.

Accordingly, the present invention provides a process for the synthesis of polyol fatty acid polyesters wherein a substantially solvent-free reaction mixture of a polyol and/or fatty acid oligoesters thereof, a fatty acid lower-alkylester, a transesterification catalyst, and an emulsifier selected from the group of alkali metal soaps, is caused to react under transesterification conditions, the process comprising the step of a substantial reduction of the alkali metal soap level during the transesterification reaction at a degree of conversion of from 15 to 60%.

Preferably, the soap is removed at a degree of conversion of from 20 to 50%, and most preferably at a degree of conversion of from 30 to 45%.

By "substantial reduction" is meant a reduction to a level of less than 50% by weight of the initial soap level. Under practical processing conditions reductions to residual soap levels of within the range of 10 to 40% are preferred.

The reduction of the soap level in the reaction mixture may be carried out by any suitable refining method. Such methods in particular include mechanical techniques, such as separation by centrifuge, hydrocyclon or filter, of that part of the soap already separated out, but also conventional washing methods with aqueous, optionally electrolyte containing, solutions which may have pH-values ranging from neutral to high alkaline, in particular pH-values of over 12, followed by drying, as well as acidification and subsequent removal of the free fatty acids by way of e.g. steam-refining or molecular distillation. If necessary the soap removal step should be followed by a drying step to substantially remove any water introduced during the soap reduction step.

After the substantial reduction of the soap it is desirable to introduce into the mixture a supplementary amount of transesterification catalyst. In particular, the alkali metal salts of lower alkyl alcohols have been found suitable, such as sodium methanolate. Suitable supplementary amounts are within the range of from 0.1 to 2% by weight of the reaction mixture, amounts within the range of from 0.15 to 0.5% being preferred.

The transesterification reaction is suitably carried out at a temperature within the range of from 100° to 180° C. Preferred temperatures are within the range of from 110° to 160° C., the range of from 120° to 150° C. being preferred most.

In general the transesterification reaction is carried out under conditions of reduced pressure so as to remove the lower-alkyl alcohol formed from the fatty acid lower-alkylester during the transesterification. Particular pressure conditions are a resultant of both process-technical and economic considerations. During the final stage of the reaction it is preferred to apply pressures as low as possible within the constraints of economic processing in order to drive the transesterification to high degrees of conversion. Preferred pressures during the final stage are below 25 mbar or even below 5 mbar.

However, during the initial stage of the reaction it is of advantage to control the pressure to a level of within 30 mbar, most preferably within 15 mbar from the equilibrium vapour pressure of the lower-alkyl alcohol corresponding to a degree of conversion within the range of from 10 to 30% in order to avoid that part of the polyol present in the reaction mixture at the start of the transesterification reaction remains unreacted throughout the reaction. Only at the very start of the transesterification reaction the pressure may be reduced to a level as low as possible, such as e.g. a level of below 25 mbar or even 10 mbar, in order to start-up the reaction.

The pressure immediately after the start-up is preferably controlled to a level within the range of from 60 to 150 mbar, preferably 90 to 125 mbar during said initial stage.

It is preferred to apply agitation to the reaction mixture, in particular throughout the initial stage of the reaction e.g. by way of stirring means in the reaction vessel.

In view of the difference in pressure regime during the initial and final stage of the reaction it may be of advantage to use a reaction system comprising two separate reaction vessels each equipped with pressure control means optimised to the specific reduced pressure regime needed. In this way very expensive pressure control means capable of coping with a wide range of pressures and quantities of lower-alkyl alcohol to be removed can be avoided.

Suitably, the lower-alkyl alcohol formed during the transesterification reaction from the lower-alkylester is condensed in suitable condenser means after the removal thereof from the reaction mixture, and collected for subsequent use or re-use.

In general the reactants used in the transesterification reaction in accordance with the process of the present invention comprise a polyol and/or fatty acid oligoester thereof, a fatty acid lower alkylester, a transesterification catalyst, and an emulsifier selected from the group of alkali metal soaps. In the preparation of the mixture of reactants also solvents, such as water and/or lower-alkyl alcohols, may optionally be introduced separate from or together with one or more of these reactants.

The polyol can be any of those as defined hereinbefore, or a mixture thereof. Preferred polyol starting materials are the sugar polyols, and in particular sucrose. The polyol starting material does not necessarily consist solely of non-esterified polyols. It may in addition or instead comprise polyol oligoesters of fatty acids, such as mono-, di- and/or triesters, which are intermediates in the conversion of polyols to the polyol fatty acid polyesters.

Suitable fatty acid lower-alkylesters are fatty acid esters of the group of lower alcohols including mono-, di- and triols. In particular, the ester is derived from the $C_1$–$C_5$ mono-alcohols, preferably methanol. The fatty acid residues can be any of those as defined hereinbefore, the selection of which is dependent of the specific polyol fatty acid esters desired.

The amount of fatty acid lower-alkylester is dependent on the desired degree of conversion. In the synthesis of polyol polyesters having high degrees of conversion in general excess amounts of fatty acid lower-alkylester are used. More particularly, when fully converted sucrose polyesters are aimed at, good results are obtained when a molar ratio of fatty acid lower-alkylester : sucrose is used within the range of from 10:1 to 20:1, in particular, of from 10:1 to 15:1. or even 10:1 to 14:1.

Suitable transesterification catalysts include the group consisting of alkali metals, alkaline earth metals, and alloys thereof, as well as the alkoxides, bicarbonates, carbonates, hydrides, and hydroxides of such metals. KOH has been found to be particularly suitable, but also NaOH and the corresponding carbonates, and bicarbonates of potassium or sodium can be advantageously used. Although one might argue that the above reagents are not the catalysts themselves, but are reagents forming the catalyst, in this specification as is done in the literature relating to similar processes, this group will be referred to as catalysts.

The catalyst is used in an amount corresponding to a molar ratio of catalyst : polyol of at least 0.01:1, and preferably of 0.05:1 to 1:1.

The reaction mixture further comprises an emulsifier selected from the group consisting of alkali metal soaps derived from any of the fatty acids as defined hereinbefore. It has been found that conversion rates of polyol to polyol fatty acid ester are improved when fatty acid soap emulsifiers are used comprising at least 15%, but preferably even at least 75% of short chain fatty acid soap. Such short chain fatty acid soap is characterized by a fatty acid chain length of less than 15 carbon atoms, and in particular within the range of 6 to 12 carbon atoms, such as coconut soap.

It has also been found convenient to introduce the alkali metal soap emulsifier into the reaction mixture in the form of a precursor thereof, such as the corresponding free fatty acids. In such a case the composition of the reactant mixture should be such that the precursor is converted into the corresponding alkali metal soap after addition to and mixing with the reactant mixture.

When free fatty acids are used as emulsifier precursors, an alkaline material should be present in the reaction mixture suitable to convert the fatty acid precursor into the corresponding soap emulsifier. Suitably, the transesterification catalyst can be used to effectuate such a conversion. Accordingly, the amount of catalyst should be sufficient to ensure both proper catalytic action during the esterification, as discussed hereinbefore, and full neutralization of such a soap precursor to the corresponding soap.

Suitable amounts of emulsifier lie within the range of from 0.1 to 15% by weight, preferably of from 0.1 to 12%, and most preferably of from 0.2 to 6% by weight of the total reactant mixture.

Optionally, one or more solvents may be introduced separate from or together with the various reactants to improve addition and mixing thereof. Suitable solvents include water and/or lower alcohols, such as $C_1$–$C_5$ alcohols, in particular methanol. The solvent is subsequently removed before or at the start of the transesterification reaction.

Advantageously, the reaction mixture is spray-dried before starting the esterification reaction to achieve a homogenized and substantially solvent-free reaction mixture particularly suitable as starting mixture for the subsequent esterification in accordance with the present invention.

In this specification the term "homogenized" means intimately mixed and is not restricted to homogenized in a narrow microscopic sense.

By "substantially solvent-free" is meant comprising less than 0.5% of solvent. Solvent levels at the start of the esterification reaction of less than 0.1, or even 0.05% are preferred.

Spray-drying is suitably effected by passing the initial mixture of reactants through a spraying nozzle into a drying chamber. Intimate mixing occurs due to the dissipation of energy on passing through the spraying nozzle. Evaporation of the solvent occurs in the drying chamber, the resulting vapour continuously being removed from the drying chamber by suitable reduced pressure or gas flow conditions. Adequate solvent evaporation may be established by a variety of per se conventional techniques, including the application of reduced pressure and/or elevated temperature conditions, or the use of, optionally heated, co-current, counter-current or mixed-current inert gas flows.

In a batch-wise operation the drying chamber is also suitably used as reaction vessel for the transesterification reaction. In a continuous or semi-continuous operation the drying chamber and reaction vessel preferably are separate.

It may be of further advantage to pre-mix the reactants before passing through the spraying nozzle by an alternative agitation step for example employing a dynamic or static mixer, or flow restriction in the feed line to the spraying nozzle.

It is preferred to prepare the reactant mixture by way of the following process.

In an initial step the polyol or the fatty acid oligoester thereof is mixed with the catalyst in a liquid system so as to form the corresponding polyol anion. The formation of the actual polyol anion may be immediate or only be realized under substantially solvent-free conditions. Preferably, the contact between the polyol or the oligoester thereof and the catalyst are mixed in the presence of a solvent, which is subsequently removed in the spray-drying step in accordance with the present invention. Most preferably, the polyol or the oligoester thereof and the catalyst are first partially or fully dissolved in a solvent and subsequently mixed. Suitable such solvents include water, lower alcohols and mixtures thereof. In particular water is a suitable solvent if potassium or sodium hydroxide is used as the transesterification catalyst.

In a subsequent step this liquid system is added to the fatty acid lower-alkylester, optionally in combination with the emulsifier. After addition to the fatty acid lower-alkylester the resulting reaction mixture may be conveniently spray-dried.

Although alkali metal soaps or suitable precursors thereof are suitable emulsifiers in terms of the esterification reaction a drawback that may be attached to the use of soaps is the fact that the spray-drying thereof necessitates relatively frequent cleaning of the spray-drying equipment. In particular on a technical scale this is undesirable.

Accordingly, it is preferred to add the soap emulsifiers or precursors thereof, to the reaction mixture only after the spray-drying step. Using this route the relatively frequent cleaning of the spray-drying equipment can be avoided.

The degree to which desolvatization is achieved in the spray-drying step, is the resultant of economic and process-technical factors, such as in particular the amount of solvent to be removed and the corresponding energy input or temperature required in the drying chamber.

Accordingly, instead of using spray-drying conditions resulting in full removal of solvent, it may be of advantage to have the spray-drying step followed by a further 'post-drying' treatment which drives the removal of residual solvent to substantial completion. Any such conditions resulting in evaporation of any residual solvent still present after spray-drying or introduced in the post spray-drying addition of the emulsifier component, may be suitable and include temperature and reduced pressure conditions, stripping with suitable stripping agents, such as preferably methanol, or inert gases, such as nitrogen, or submitting the reaction mixture to a further spray-drying step.

Preferably, the reaction mixture is submitted to conditions of elevated temperature and reduced pressure suitable for drying. Drying temperatures lie below about 110° C., and preferably within the range of 60° to 100° C. Suitably, these post-drying conditions are maintained for periods of up to several hours, periods of 0.5 to 3 hours being preferred.

Suitably the solvent level of the reaction mixture is reduced to below 0.5% in the spray-drying step and further reduced to below 0.1% in the subsequent post-drying step. Preferably, the solvent level is reduced to below 0.1% in the spray-drying step and to below 0.05% in the post-drying step.

If so desired a supplementary amount of polyol may be introduced into the starting mixture of reactants before starting the transesterification reaction.

Although the process of the present invention is suitable for the synthesis of polyol fatty acid esters of the general group as defined hereinbefore, it is particularly suitable for the synthesis of polyol fatty acid polyesters esterified to at least 95% degree of conversion, preferably derived from the sugar polyols selected from the group of disaccharides or the alcohol derivatives thereof, such as sucrose.

Preferred embodiments of the invention will now be illustrated with reference to the following examples, all percentages being by weight unless indicated otherwise.

Example 1

An intimate mix of 89.2 parts by weight of distilled fatty acid (soybean) methylester, 3.2 parts by weight of potassium coconut soap and 2.0 parts by weight of potassium sucrate was prepared by spray-drying. A further 5.5 parts by weight of sucrose was dispersed into this mixture.

Subsequently, the mixture of reactants was heated to 130°–135° C., and the pressure reduced to a level of about 5 mbar. After about 15 minutes the sucrose started to react under formation and evaporation of methanol causing slight foaming. At this point of time the pressure was allowed to gradually (in about 15 minutes) increase to about 100 mbar. The pressure was maintained at this level for about 3 hours, after which period the reaction mixture was homogeneous (no unreacted sucrose) and the degree of conversion had reached a value of about 35% as calculated from the OH-value.

The transesterification reaction was then stopped by cooling down the reaction mixture to below 100° C. The reaction mixture was then submitted to six subsequent washings with 15% of water at 90° C. neutralised and dried. At this point the soap level had been reduced to a level of about 1.6% by weight of the reaction mixture. A supplementary amount of 0.15% by weight of sodium methanolate was introduced by way of a solution of 30% sodium methanolate in methanol.

Subsequently the temperature was raised to about 135° C. and the pressure reduced to a level of below 5 mbar. After only 15 minutes the degree of conversion had reached a level of 89% resulting after a further two hours in a degree of conversion of over 95%.

We claim:

1. In a process for the synthesis of polyol fatty acid polyesters wherein a substantially solvent-free reaction mixture of a polyol, a fatty acid lower-alkylester, a transesterification catalyst, and an emulsifier selected from the group of alkali metal soups is caused to react under transesterification conditions of reduced pressure and elevated temperature, the improvement comprising the step of removing at least 50% of the initial amount of the alkali metal soap from the reaction mixture when the degree of conversion of the transesterification reaction is from 15 to 60%.

2. A process according to claim 1 wherein the soap is removed at a degree of conversion of from 20 to 50%.

3. A process according to claim 1 wherein the soap level is reduced to within the range of from 10 to 40% of the initial level.

4. A process according to claim 1 wherein said step is carried out by a mechanical refining technique.

5. A process according to claim 4 wherein said mechanical refining technique comprises separation by centrifuge.

6. The process according to claim 5 wherein the mechanical refining technique consists of separation by centrifuge.

7. In a process for the synthesis of polyol fatty acid polyesters wherein a substantially solvent-free reaction mixture of a polyol, a fatty acid lower-alkylester, a transesterification catalyst, and an emulsifier selected from the group of alkali metal soaps is caused to react under transesterification conditions of reduced pressure and elevated temperature, the improvement comprising the step of removing at least 50% of the initial amount of the alkali metal soap from the reaction mixture when the degree of conversion of the transesterification reaction is from 15 to 60%, and the subsequent step of introducing into the reaction mixture a supplementary amount of from 0.1 to 2% of a transesterification catalyst calculated by weight of the reaction mixture.

8. A process according to claim 7 wherein said supplementary amount of transesterification catalyst is within the range of from 0.15 to 0.5% by weight.

9. In a process for the synthesis of sucrose fatty acid polyesters having a degree of conversion of at least 95% wherein a substantially solvent-free reaction mixture of a sucrose, a fatty acid lower-alkylester, a transesterification catalyst, and an emulsifier selected from the group of alkali metal soaps is caused to react under transesterification conditions of reduced pressure and elevated temperature, the improvement comprising the step of removing at least 50% of the initial amount of the alkali metal soap from the reaction mixture when the degree of conversion of the transesterification reaction is from 15 to 60%.

10. In a process for the synthesis of sucrose fatty acid polyesters having a degree of conversion of at least 95% wherein a substantially solvent-free reaction mixture of a sucrose, a fatty acid lower-alkylester, a transesterification catalyst, and an emulsifier selected from the group of alkali metal soaps is caused to react under transesterification conditions of reduced pressure and elevated temperature, the improvement comprising the step of removing at least 50% of the initial amount of the alkali metal soap from the reaction mixture when the degree of conversion of the transesterification reaction is from 15 to 60%, and the subsequent step of introducing into the reaction mixture a supplementary amount of from 0.1 to 2% of a transesterification catalyst calculated by weight of the reaction mixture.

* * * * *